United States Patent [19]
Hayashi

[11] Patent Number: 5,777,344
[45] Date of Patent: Jul. 7, 1998

[54] OPHTHALMIC APPARATUS

[75] Inventor: Akihiro Hayashi, Toyokawa, Japan

[73] Assignee: Nidek Co., Ltd., Aichi, Japan

[21] Appl. No.: 867,449

[22] Filed: Jun. 2, 1997

[30] Foreign Application Priority Data

Jun. 28, 1996 [JP] Japan ................................. 8-188566
Apr. 30, 1997 [JP] Japan ................................. 9-127878

[51] Int. Cl.⁶ ........................................................ A61B 3/00
[52] U.S. Cl. ........................................... 351/245; 351/211
[58] Field of Search .................................... 351/243, 245,
351/237, 246, 205, 200, 211

[56] References Cited

U.S. PATENT DOCUMENTS 5,444,504  8/1995  Kobayashi et al. .................... 351/237

FOREIGN PATENT DOCUMENTS

A-6339462  12/1994  Japan .

*Primary Examiner*—Hung X. Dang
*Attorney, Agent, or Firm*—Oliff & Berridge PLC

[57] ABSTRACT

An ophthalmic apparatus comprises an optical unit for changing-over and disposing optical elements having various kinds of optical characteristics to an inspection window, holding device for holding the optical unit, gyrating device for making the holding device gyrate between an evacuation position and an inspection position, vertical motive device for making the holding device move vertically, and locking device for preventing electromagnetically the holding device from working.

12 Claims, 4 Drawing Sheets

OPHTHALMIC APPARATUS

BACKGROUND OF THE INVENTION

1. Field of the Invention

The present invention relates to an ophthalmic apparatus having a subjective refractive power measuring device, and more particularly, relates to mechanism for making the subjective refractive power measuring device gyrate and move vertically.

2. Description of Related Art

As an ophthalmic apparatus for use in the spectacles prescription and the vision inspection or the like, such a subjective refractive power measuring apparatus is known that has a disc plate which is provided with a lot of lens, and a right and left optical unit which changes over and disposes an optical system of desired optical characteristics to an inspection window. This optical unit is disposed at an evacuation position when it is not used, and disposed just in front of an eye of an examinee when it is used. It is also moved in vertical direction relative to a position of the eye to be examined.

Therefore, generally the optical unit is held by an arm fixed to a poll which is held so that it can gyrate and move vertically. And, the poll is locked by fastening tight by a motor so as not to gyrate and not to move vertically.

However, referring to the above-mentioned lock mechanism, such troubles concerning adjustment occur that torque is made to be in insufficient when the centering adjustment is insufficient, also, the lock does not come back due to friction when motor rotation is too high. These lock mechanisms are slow in response.

SUMMARY OF THE INVENTION

The present invention has been made in view of the above circumstances and has an object to overcome the above problems and to provide an ophthalmic apparatus for which the adjustment concerning lock mechanism of gyration and vertical motion may be easier, or to provide an ophthalmic apparatus which does not need adjusting.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus of this invention comprises optical unit for changing-over and disposing optical elements having various kinds of optical characteristics to an inspection window, holding means for holding the optical unit, gyrating means for making the holding means gyrate between an evacuation position and an inspection position, vertical motive means for making the holding means move vertically, and locking means for preventing electromagnetically the holding means from working.

In another aspect of the present invention, an ophthalmic apparatus comprises inspection table, subjective refractive power measuring device of which an inspection window is provided with optical elements having various kinds of optical characteristics so as to be free to be changed-over, supporting parts for supporting the subjective refractive power measuring device so as to be able to gyrating and moving vertically about the inspection table, and electromagnetic locking means for preventing electromagnetically at least one of gyration and vertical motion of the subjective refractive power measuring device which is supported by the supporting parts from working.

Further, in another aspect of the present invention, an ophthalmic apparatus comprises inspection table, subjective refractive power measuring device of which an inspection window is provided with optical elements having various kinds of optical characteristics so as to be free to be changed-over, supporting parts for supporting the subjective refractive power measuring device so as to be able to gyrating and moving vertically about the inspection table, electromagnetic locking means for use in gyration for preventing electromagnetically the subjective refractive power measuring device which is supported by the supporting parts from gyrating, and electromagnetic locking means for use in vertical motion for preventing electromagnetically the subjective refractive power measuring device which is supported by the supporting parts from moving vertically.

According to the present invention, it is capable of adjusting the mechanism of gyration and vertical motion of arm part, furthermore the lock and the cancellation of the lock for gyration and vertical motion can be performed quickly with easy operation.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

A detailed description of one preferred embodiment of an ophthalmic apparatus embodying the present invention will now be given referring to the accompanying drawings.

Figure 1:
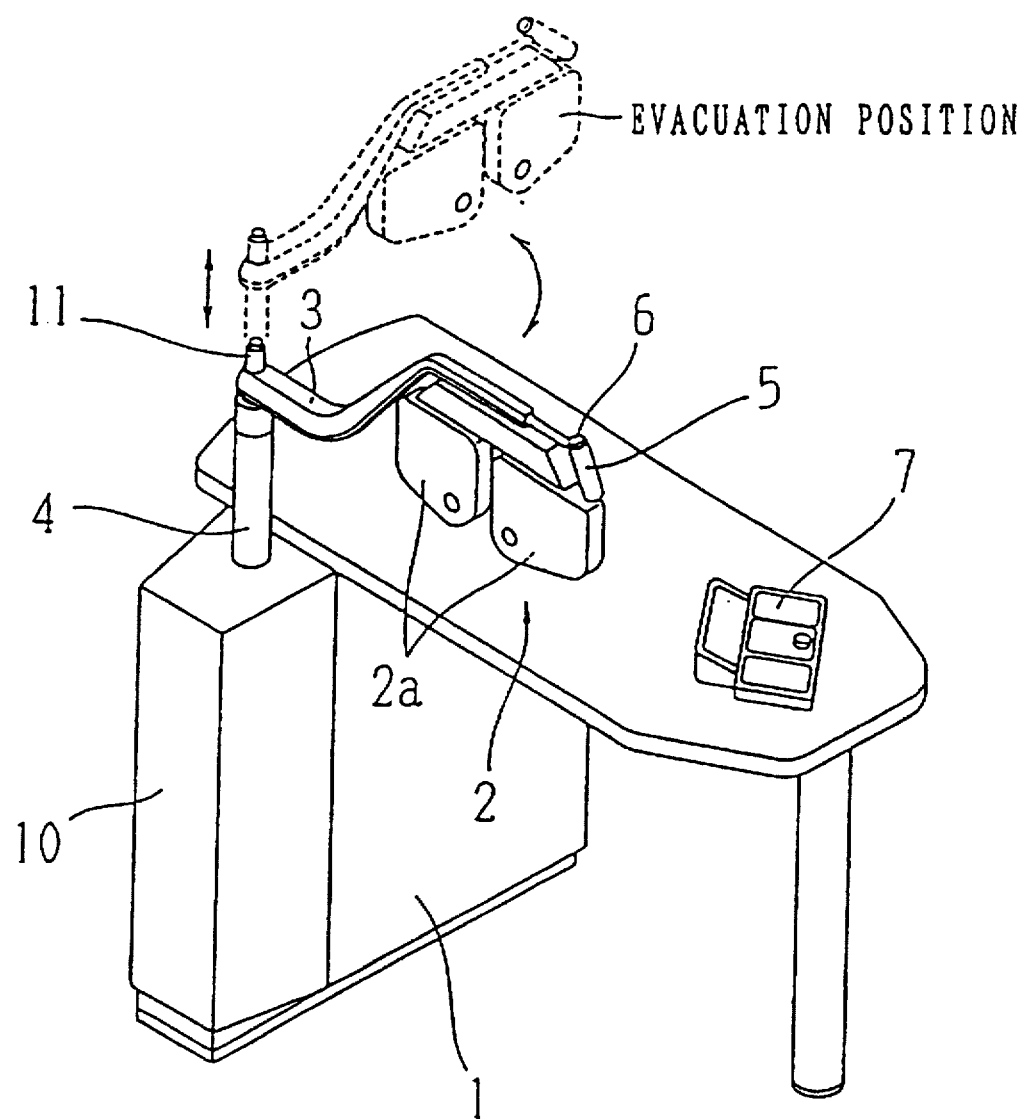
FIG. 1 is an overview showing a whole schematic configuration of an ophthalmic apparatus of the preferred embodiment.

In FIG. 1, there is shown the overview of the preferred embodiment.

Reference numeral 1 denotes an inspection table, and 2 denotes a subjective refractive power measuring device which changes-over and disposes various kinds of optical elements to an inspection window. An optical unit 2a included by a subjective refractive power measuring device 2 is held by an arm part 3 which is fixed to a poll 11. The poll 11 is supported by a strut part 4 so as to gyrate and move vertically. The arm part 3 is provided with a grip part 5 and a moving instruction switch 6 which are used at the time when the optical unit 2a is made to move between an inspection position and an evacuation position (denoted by dotted line). Reference numeral 7 denotes a control box which changes-over various kinds of optical elements in the subjective refractive power measuring device 2, and changes-over targets of a device which indicates a vision chart (not shown).

Figure 2:
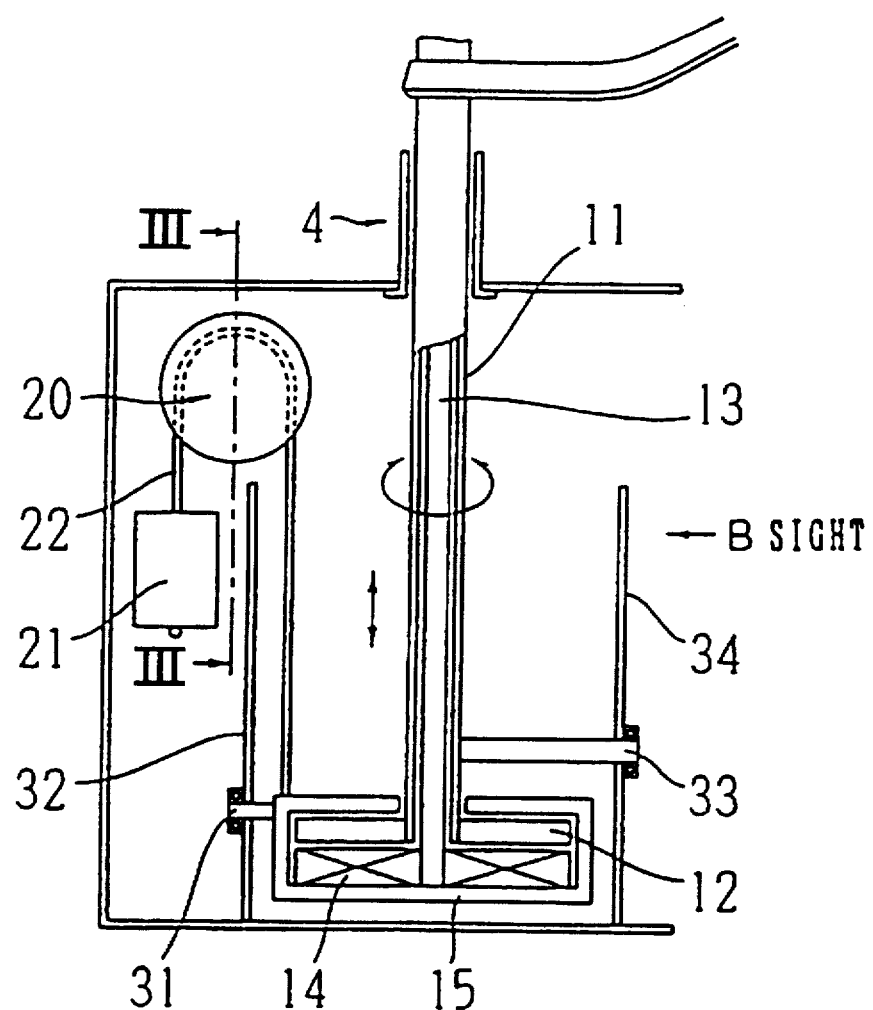
FIG. 2 is a view showing a section of an important part of mechanism of gyration and vertical motion of an arm part of an ophthalmic apparatus of the preferred embodiment.

FIG. 2 is a view showing a section of an important part of mechanism of gyration and vertical motion of the arm part of the ophthalmic apparatus of the preferred embodiment.

The poll 11 supports the arm part 3. The poll 11 is provided so as to rotate about a supporting shaft 13 through which the poll 11 is inserted. An illumination unit which is not shown is provided for the upper edge of the supporting shaft 13 to illuminate the surface of the table. A brake disc 12 which is disc-shaped is fixed to the lower part of the poll 11. 14 denotes a positive type electromagnetic brake which generates magnetic force while electricity is supplied, and some gaps are provided between a positive type electromagnetic brake and a brake disc 12. Rotation of the brake disc 12 is locked by magnetic force due to power-on of the electromagnetic brake 14. 15 denotes a holder to which the supporting shaft 13 and the electromagnetic brake 14 are fixed. The holder 15 is fixed so as not to rotate, allowing the holder 15 to move vertically together with the poll 11. Even if the poll 11 gyrates together with the arm part 3, the supporting shaft 13 does not rotate due to the fixation to the holder 15, therefore the illumination unit provided for the supporting shaft 13 can always illuminate the surface of the table. Also, the supporting shaft 13 may be omitted in the case that the illumination unit is not provided.

20 denotes a brake mechanism for vertical motion which is mentioned below. 21 denotes a weight having nearly the same weight as total weight of the subjective refractive power measuring device 2, the arm part 3, the poll 11, the holder 15 and so on, which makes the motion of the arm part easy, and 22 denotes a wire which connects the weight 21 and the holder 15.

Figure 3:
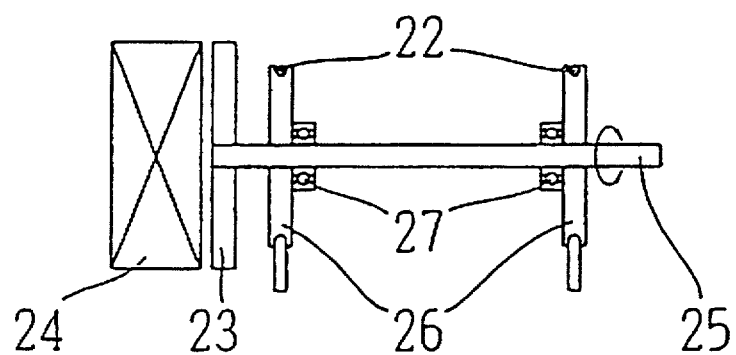
FIG. 3 is a view showing a section of A—A line in FIG. 2 showing a configuration of mechanism of a vertical motive brake.

FIG. 3 is a view showing a section of A—A line in FIG. 2 which shows a configuration of a brake mechanism of vertical motion 20. 23 denotes a brake disc, 24 denotes a positive type electromagnetic brake, 25 denotes a rotation shaft, 26 denotes a pulley, and 27 denotes a bearing. Some gaps are provided between the brake disc 23 and the electromagnetic brake 24, once the electromagnetic brake 24 is under the power-on state, rotation of the brake disc 23 is locked due to magnetic force thereof. That is, vertical motion of the poll 11 and the holder 15 is locked. The wire 22 is disposed within the groove of the pulley 26, the weight 21 is held by two wires 22s.

Figure 4:
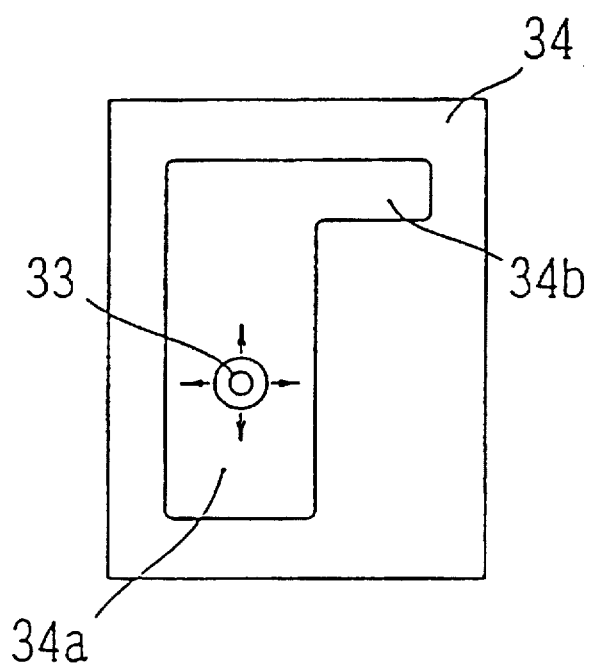
FIG. 4 is a view from B sight in FIG. 2 showing a moving guide for use in restricting a gyration range; and, FIG. 5 is a view showing an important part of a configuration of a control system of an ophthalmic apparatus of the preferred embodiment.

31 denotes a guide roller for vertical motion which is fixed to holder 15. 32 denotes a vertical direction guide which is used by the roller 31 so that the roller 31 can move only to vertical direction. 33 denotes a roller which is fixed to the poll 11, and 34 denotes a moving guide for use in restricting the gyration range (see FIG. 4 which is a view from B sight in FIG. 2).

Referring to FIG. 4, the roller 33 is free to move within an inverted L-shaped space which is provided for the moving guide 34, the poll 11 and the arm part 3 also move altogether. 34a has a wider width than the roller 33, and moves an appropriate range of not only a vertical direction but also a lateral direction. The roller 33 moves an appropriate range of a lateral direction whereby adjustment corresponding to a body shape of an examinee can be performed. The part 34b is a space at which the roller 33 is disposed in the case that the arm part 3 is at an evacuation position, which is wider than 34a. That is, when the roller 33 is disposed at the part 34a, the arm part 3 can not be made to gyrate to the evacuation position.

Figure 5:
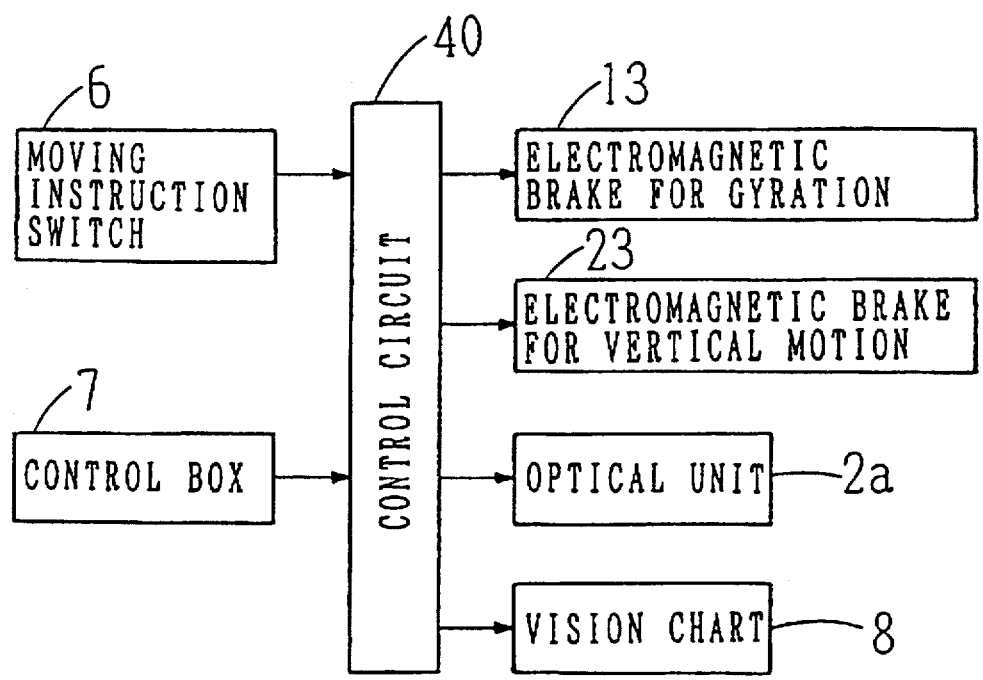

The operation of the apparatus having such architecture as described above will be described below with reference to FIG. 5.

An examiner turns on the main power supply by using a main switch which is not shown, and makes the examinee sit down in front of the table, then moves the optical unit 2a from the evacuation position to the front of the examinee. In the case that the lock mechanism for gyration and vertical motion is working, the examiner presses the moving instruction switch 6 and a control circuit 40 stops supplying electricity to the electromagnetic brakes 14 and 24, the arm part 3 comes to be free to move. The examiner rotates the optical unit 2a by holding the grip part 5, then disposes the optical unit 2a at an appropriate position corresponding to the eye to be examined. Also, the total weight of the poll 11 and so on is balanced with the weight 21 in general, therefore the optical unit 2a can be moved easily with weak force.

Once the optical unit 2a is disposed at the appropriate position corresponding to the eye to be examined, the examiner presses the moving instruction switch 6 again, thereby the control circuit 40 supplies electricity to the electromagnetic brake 14 which is fixed to the holder 15 and the electromagnetic brake 24. The electromagnetic brake 14 under power-on state generates magnetic force and fixes the brake disc 12 to prevent the poll 11 and the arm part 3 from gyrating. As the same way, the electromagnetic brake 24 for vertical motion fixes the brake disk 23 to prevent the poll 11 and the arm part 3 from moving vertically.

In the case that the examiner desires to move the arm part 3, it is moved easily only by pressing the moving instruction switch 6, and in the case that the examiner desires to fix it, it is fixed easily only by pressing the moving instruction switch 6.

According to the preffered embodiment, difficult adjustment and troubles are improved by using electromagnetic brakes. Furthermore, in the case that the power supply is not turned on, the arm part 3 can be moved since electricity does not supplied, resulting that an installation of the apparatus comes to be easier.

The present invention may be embodied in other specific forms without departing from the spirit or essential characteristics thereof. For instance, positive type electromagnetic brakes are used as the electromagnetic brakes 14 and 24, instead of these brakes, negative type electromagnetic brakes may be used for both of them. Referring to the negative type electromagnetic brakes, the brakes works on power-off state, thereby the poll 11 and arm part 3 can be fixed, therefore it is convenient when the examiner wants to fix the one or both of vertical motion and gyration in the case of carrying or power-off state.

Also, necessary electric power capacity can be reduced to the half by making the one of the electromagnetic brakes 14 and 24 be a positive type electromagnetic brakes and by making the other one of them be a negative type electromagnetic brake due to that an electromagnetic device comes to be only one that should be supplied with electricity in the case of both fixation and non-fixation of the arm part 3.

Furthermore, above-mentioned preferred embodiment, ON/OFF switch is used, in the case that the arm part 3 is moved, such switch may be used that it is continued pressing upon making the arm work.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications are suited to the particular use contemplated. It is intended that the scope of the invention be defined by the claims appended hereto, and their equivalents.

What is claimed is:

1. An ophthalmic apparatus comprising:

optical unit for changing-over and disposing optical elements having various kinds of optical characteristics to an inspection window;

holding means for holding said optical unit;

gyrating means for making said holding means gyrate between an evacuation position and an inspection position;

vertical motive means for making said holding means move vertically; and locking means for preventing electromagnetically said holding means from working.

2. An ophthalmic apparatus according to claim 1, wherein said locking means consists of an electromagnetic brake of positive type which works while electricity is supplied.

3. An ophthalmic apparatus according to claim 1, wherein said locking means is constituted of a vertical motion locking means and a gyration locking means, and at least one of them is an electromagnetic brake of positive type.

4. An ophthalmic apparatus according to claim 1, further comprising a lock canceling means.

5. An ophthalmic apparatus according to claim 1, wherein said locking means consists of an electromagnetic brake of negative type which works while electricity is not supplied.

6. An ophthalmic apparatus according to claim 1, wherein said locking means is constituted of a vertical motion locking means and a gyration locking means, and at least one of them is an electromagnetic brake of negative type.

7. An ophthalmic apparatus comprising:

inspection table;

subjective refractive power measuring device of which an inspection window is provided with optical elements having various kinds of optical characteristics so as to be free to be changed-over;

supporting parts for supporting said subjective refractive power measuring device so as to be able to gyrating and moving vertically about said inspection table; and electromagnetic locking means for preventing electromagnetically at least one of gyration and vertical motion of said subjective refractive power measuring device which is supported by said supporting parts from working.

8. An ophthalmic apparatus according to claim 7, wherein said electromagnetic locking means consists of a brake disc and an electromagnetic brake.

9. An ophthalmic apparatus according to claim 7, further comprising a lock canceling means for canceling the motion of subjective refractive power measuring device which is prevented by said electromagnetic locking means.

10. An ophthalmic apparatus comprising:

inspection table;

subjective refractive power measuring device of which an inspection window is provided with optical elements having various kinds of optical characteristics so as to be free to be changed-over;

supporting parts for supporting said subjective refractive power measuring device so as to be able to gyrating and moving vertically about said inspection table;

electromagnetic locking means for use in gyration for preventing electromagnetically said subjective refractive power measuring device which is supported by said supporting parts from gyrating; and electromagnetic locking means for use in vertical motion for preventing electromagnetically said subjective refractive power measuring device which is supported by said supporting parts from moving vertically.

11. An ophthalmic apparatus according to claim 10, wherein respective said electromagnetic locking means for use in gyration and said electromagnetic locking means for use in vertical motion consist of a brake disc and an electromagnetic brake.

12. An ophthalmic apparatus according to claim 10, further comprising a lock canceling means for canceling both gyration and vertical motion of subjective refractive power measuring device which is prevented by said electromagnetic locking means for use in gyration and said electromagnetic locking means for use in vertical motion.

* * * * *